United States Patent [19]

Kamienski

[11] Patent Number: 4,748,283
[45] Date of Patent: May 31, 1988

[54] HYDROCARBON AND CHLORINATED HYDROCARBON-SOLUBLE MAGNESIUM DIALKOXIDES

[75] Inventor: Conrad W. Kamienski, Gastonia, N.C.

[73] Assignee: Lithium Corporation of America, Bessemer City, N.C.

[21] Appl. No.: 15,388

[22] Filed: Feb. 17, 1987

[51] Int. Cl.$^4$ .................. C07C 31/30; C07F 05/05
[52] U.S. Cl. .................... 568/851; 556/170; 556/181; 556/187; 568/678; 568/679; 568/715
[58] Field of Search .............. 568/851, 841, 715, 678, 568/679, 840; 556/187, 170

[56] References Cited

U.S. PATENT DOCUMENTS

| | | | |
|---|---|---|---|
| 3,094,546 | 6/1963 | Tpwers | 568/851 |
| 3,239,568 | 3/1966 | De Pree et al. | 568/851 |
| 3,294,770 | 12/1966 | Ragazzini et al. | 568/851 |
| 3,657,361 | 4/1972 | Lenz et al. | 568/851 |
| 3,803,250 | 4/1974 | Hartmann | 568/851 |
| 3,920,713 | 11/1975 | Feichtinger et al. | 568/851 |
| 3,971,833 | 7/1976 | Lenz et al. | 568/851 |
| 4,027,089 | 5/1977 | Aishima et al. | 568/851 |
| 4,127,507 | 11/1978 | Fannin et al. | 260/665 R |
| 4,133,824 | 1/1979 | Maipass et al. | 568/851 |
| 4,222,969 | 9/1980 | Fannin et al. | 260/665 R |
| 4,327,230 | 4/1982 | Ackermann et al. | 568/851 |
| 4,410,742 | 10/1983 | Mueller | 568/851 |
| 4,421,936 | 12/1983 | Smith et al. | 568/851 |
| 4,555,498 | 11/1985 | Kamienski | 568/851 |
| 4,634,786 | 1/1987 | Kamienski | 568/851 |

FOREIGN PATENT DOCUMENTS

| | | | |
|---|---|---|---|
| 2612642 | 9/1977 | Fed. Rep. of Germany | 568/851 |
| 7711923 | 5/1979 | Netherlands | 568/851 |
| 727923 | 4/1955 | United Kingdom | 568/851 |
| 767601 | 2/1957 | United Kingdom | 568/851 |

Primary Examiner—Werren B. Lone
Attorney, Agent, or Firm—Sidney Wallenstein; Harry V. Strampel

[57] ABSTRACT

Stable liquid hydrocarbon-soluble novel magnesium dialkoxide compositions useful as or in the preparation of polymerization catalysts and initiators for the polymerization of alpha-olefins and diolefins are prepared, for instance, by reacting certain organomagnesium compounds in liquid hydrocarbon solvents with (a) aliphatic, cycloaliphatic or acyclic beta- and gamma-alkyl-substituted $C_5$–$C_{18}$ monohydric secondary and tertiary alcohols; or (b) mixtures of (a) with beta- and/or gamma-alkyl-unsubstituted $C_3$–$C_{18}$ aliphatic secondary or tertiary alcohols; or (c) mixtures of (a) with $C_1$–$C_{18}$ aliphatic primary linear alcohols. Such dialkoxides, and complexes thereof, soluble in hydrocarbon or chlorinated hydrocarbon solvents, can be reacted with triorganoaluminum compounds such as, for instance, TIBAL, organolithium, or organopotassium compounds, e.g., alkyllithiums, or alkali metal alkoxides. An illustrative example of the novel magnesium dialkoxides is magnesium bis-2,3-dimethyl-3-pentyloxide.

17 Claims, No Drawings

HYDROCARBON AND CHLORINATED HYDROCARBON-SOLUBLE MAGNESIUM DIALKOXIDES

TECHNICAL FIELD

BACKGROUND OF THE INVENTION

This invention is directed to certain novel magnesium dialkoxides and to complexes thereof and to processes for the preparation thereof.

In recent years, certain alkylmagnesium alkoxides and magnesium dialkoxides have been found to possess utility as precursors for magnesium chloride support materials utilized in the preparation of Ziegler-Natta catalysts for alpha-olefin polymerization.

For example, ethylene has been polymerized at 80° C. in hexane using a magnesium alcoholate-TiCl$_4$ reaction product (MgCl$_2$) and a trialkylaluminum as the catalyst system. (M. Bahadir, S. Lutze, W. Payer, P. Schneller, Ger. Offen. DE No. 3,120,186, Dec. 9, 1982, to Ruhrchemie.). In another application, solid magnesium diethoxide, suspended in carbon tetrachloride, is treated with ethyl benzoate and titanium tetrachloride, and the resulting solid product is used in combination with trialkylaluminum and p-methoxybenzoate as a catalyst to polymerize propylene (B. L. Goodall, A. vander Nat, and W. Sjardyn, U.S. Pat. No. 4,414,132, to Shell Oil Co.; also U.S. Pat. No. 4,216,383).

Certain alkylmagnesium alkoxides and magnesium dialkoxides have also been generated by reaction of complexed magnesium dialkyls, coated on an inert support material, with certain alcohols. These supported magnesium dialkoxides are then further reacted with HCl and/or titanium tetrachloride to give a supported magnesium chloride catalyst which can be dried and used to polymerize ethylene (R. Hoff, U.S. Pat. No. 4,402,861; R. A. Dombro, U.S. Pat. No. 4,378,304, to Chemplex Co.; and M. Bahadir and W. Payer, Ger. Offen. DE No. 3,223,331, to Ruhrchemie.).

In still another application, a mixture of magnesium isopropoxides and aluminum isopropoxides in tetrahydrofuran (THF) (the solubility, if any, unspecified) is reacted with a solution of magnesium aluminum hydride in tetrahydrofuran to give a solution of magnesium aluminum isopropoxy hydride in THF. (S. Cucinella and G. Dozzi, Ger. Offen. DE No. 3,000,490, July 31, 1980, to Anic, Sp.A.).

Schell (U.S. Pat. No. 4,419,269) claims treating R$_2$Mg·xMR'$_x$ with alcohols of the general type R(OR'-)$_n$OH and Z(OR')$_n$ (OR")$_n$, in the presence of Al(R$^3$)$_3$X$_m$, but gives no examples, for instance, of the use of ethoxyethanol, and also not in the absence of aluminum compounds.

D. Gessell (U.S. Pat. Nos. 4,246,383; 4,387,200; 4,244,838; and 4,496,660 to Dow Chemical Company) also describes the preparation of useful alpha-olefin polymerization catalysts by reacting a dialkymagnesium compound (in the presence of at least 50 mole % of a trialkylaluminum compound) with sufficient n-propyl alcohol to convert all of the alkyl groups to n-propoxy groups, thus forming a hydrocarbon-soluble solution of magnesium and aluminum n-propoxides, followed by reaction of the resulting solution with a titanium ester and a chlorinating agent, ethylaluminum dichloride, to give a MgCl$_2$-supported titanium catalyst.

It is also known to employ a mixture of certain dialkylmagnesiums and either lithium alkoxide, sodium alkoxide, or potassium alkoxide in the polymerization and telomerization of butadiene to form low molecular weight liquid polymers, useful in the coating and also in the impregnation and encapsulation of electrical transformers and other metal parts to protect them from corrosion (C. W. Kamienski and J. F. Eastham, U.S. Pat. Nos. 3,742,077; 3,822,219; 3,847,833). Other patents describing the formation of polymeric products from similar catalyst systems are U.S. Pat. Nos. 4,139,490 and 4,429,090 (to Firestone Tire & Rubber Co.); and U.S. Pat. No. 3,716,495 (to Phillips Petroleum Co.).

Although, certain alkymagnesium alkoxides are known to be soluble in hydrocarbon solvents, as described in U.S. Pat. Nos. 4,410,742 and 4,133,824; and by G. E. Coates, J. A. Heslop, M. E. Redwood, and D. Ridley, J. Chem. Soc., 1964, 2483 (see also B. J. Wakefield in *Advances in Inorganic Chemistry and Radiochemistry*, Volume ii, 1968, page 396 (Academic Press), relatively little is known about the solubility of magnesium dialkoxides in various organic solvents. It is known that both magnesium dimethoxide and diethoxide are insoluble in ethers and hydrocarbon solvents, as described in Kirk Othmer's *Encyclopedia of Chemical Technology*, Volume 2, page 12, 3rd Edition, John Wiley, 1978. Magnesium diisopropoxide was found by D. Bryce-Smith and B. J. Wakefield (see above) to be insoluble in methylcyclohexane, benzene and ether, and only sparingly soluble in isopropanol. Magnesium di-t-butoxide is not soluble in ethyl ether (see Coates reference, as well as D. C. Bradley in *Advances in Inorganic Chemistry and Radiochemistry*, Volume 15, page 265, Academic Press), and thus, presumably, would be even less soluble in hydrocarbons. Solubility of magnesium alkoxides is not improved by the addition of aluminum alkyls (B. V. Johnson, N. M. Karayannis (European Patent Application No. 95,290, to Standard Oil Company). From the general dearth of information on magnesium dialkoxides, it would appear that these materials are, generally speaking, as a class insoluble or sparingly soluble and intractable in most organic solvents, particularly hydrocarbon or chlorinated hydrocarbon solvents.

Screttas (U.S. Pat. No. 3,932,545) discloses the preparation of hydrocarbon solvent-soluble alkali metal-containing organometallic products which are prepared by reacting an organo-alkali metal compound having an alkali metal-to-carbon bond with a di(organooxy) magnesium compound in a hydrocarbon solvent to produce a reaction product which, at least in the case where the organo-alkali metal compound is, for instance, phenyllithium or cyclohexyllithium, is more soluble in the hydrocarbon solvent than the organo-alkali metal compound. Illustrative examples of the organo-alkali metal compound are n-butyllithium, cyclohexyllithium, cyclohexylsodium, phenyllithium and phenylsodium. Illustrative examples of the di(organooxy) magnesium compound are magnesium dialkoxides such as di-n-butoxy-magnesium, di(2-methoxy-ethoxy)-magnesium, and di-(2-ethoxyethoxy)-magnesium. Among its other lack of disclosure of various facets of my present invention is the absence of any teaching or concept of the production of hydrocarbon solutions prepared by reacting a dialkylmagnesium compound with aliphatic, cycloaliphatic or acyclic beta- and/or gamma-alkyl-substituted C$_5$–C$_{18}$ secondary or tertiary alcohols, to produce magnesium dialkoxides having excellent solubility in hydrocarbon or chlorinated hydrocarbon solvents.

Aishima et al (U.S. Pat. No. 4,027,089) deals with a process of polymerizing ethylene or mixtures of ethylene and other olefins in the presence of certain catalysts, as well as with certain catalysts for use in such polymerizations. The catalysts utilized are certain hydrocarbon-soluble organoaluminum-magnesium complexes defined by a general formula which is set out, for instance, in Column 2 and claims 1 and 14 of said patent. Aishima et al recognize that, generally speaking, organomagnesium compounds are insoluble in inert hydrocarbon solvents, although certain organomagnesium compounds have heretofore been prepared which possess reasonably good solubilities in inert hydrocarbon solvents. To the extent that certain of the Aishima et al novel catalysts are of the type which comprise complexes having alkoxy groups, they comprise organoaluminum-magnesium complexes having an alkoxy group, which complexes are soluble in inert hydrocarbon solvents, and they involve reacting certain alcohols with magnesium alkyl-aluminum alkyl complexes in which the Mg/Al ratio is from 1 to 10, with a preferred range of 2 to 6. Such products are, in any event, not magnesium dialkoxides, but rather alkylaluminum alkoxides, $R_xAl(OR)_y$, mixed with alkylmagnesium alkoxides, $R_xMg(OR)_y$, where R is alkyl, in which alkoxides there is more alkyl than alkoxy present ($x > y$). These products would be expected to be considerably more soluble than the substantially pure magnesium dialkoxide products of the present invention, which may contain optionally, distinctly minor amounts of aluminum alkoxides as solubilizers, but much less than are essential and present in the complexes of the Aishima et al patent. Over and above the foregoing, in accordance with the particularly important and advantageous aspects of the present invention, only certain types of alcohols, not taught nor suggested by Aishima et al, have been found by me to produce certain novel and useful magnesium dialkoxides which are highly soluble in hydrocarbon or chlorinated hydrocarbon solvents.

Malpass et al (U.S. Pat. No. 4,133,824) discloses hydrocarbon-soluble complexes $(R'_2Mg)_m \cdot [(R'O)_2Mg]_n$ made by reacting, for instance, a di-n-alkyl-magnesium with oxygen-containing metal compounds, illustrative of which are magnesium dialkoxides or aluminum trialkoxides. Examples are complexes of di-n-butylmagnesium in heptane with magnesium diethoxide and complexes of di-n-butylmagnesium in benzene with aluminum triisopropoxide, where the ratio of m to n is at least one or greater. As a class, generally speaking, compounds or complexes of the formula $R_2Mg \cdot (RO)_2Mg$ or (RMgOR), where R is alkyl, are hydrocarbon-soluble. In contradistinction to what is disclosed in said Malpass et al patent, only very few and only particular types of alcohols on substantially complete reaction ($n < m$) in $R_2Mg)_n \cdot ((R'O)_2Mg)_m$ of the alkyl groups in $R_2Mg$) serve to provide a hydrocarbon-soluble product without any, or without a significant quantity of, aluminum also being present, as is shown below in this aspect of the present invention.

Mueller (U.S. Pat. No. 4,410,742) deals with the preparation of organomagnesium alkoxides which are free from halogen and are soluble in hydrocarbons. This is effected by reacting hydrocarbon-soluble magnesium alkyls as such or complexed with, for example, aluminum trialkyls, with magnesium dialkoxides in a mol ratio of 1:1. The patent points out that magnesium dialkoxides, which are solid and can scarcely be brought into solution, dissolve rapidly when reacted with magnesium alkyls to form clear solutions in inert polar and non-polar, e.g., hydrocarbon solvents, to produce low-viscosity concentrated solutions. Mueller does not disclose the production of magnesium dialkoxides or alkylmagnesium alkoxides in which the alkoxy-to-alkyl ratios are substantially greater than 1, which have a particularly high solubility in hydrocarbon or chlorinated hydrocarbon solvents.

Ragazzini et al (U.S. Pat. No. 3,294,770) is directed to a process of polymerizing vinyl chloride (PVC) to produce PVC with certain improved properties. This is achieved by carrying out the polymerization of vinyl chloride, in bulk or mass, or in inert solvents, which may be saturated hydrocarbons or polar solvents, in the presence of a catalyst selected from the class consisting of mono- or dialcoholates of aluminum alkyls, trialcoholates of aluminum, alkyl magnesium alcoholates, and alcoholates of lithium. Among such catalysts disclosed in this patent are $Al(C_2H_5)_2(OC_4H_9)_2$; $(C_2H_5)Al(OC_4H_9)_2$; $LiOBu$; and $(C_4H_9)Mg(OC_3H_7)$, a butylmagnesium propoxide prepared by reacting dibutyl-magnesium with one molar equivalent of n-propyl alcohol. It may be noted that, in Example No. 14 of said patent, no hydrocarbon solvent is utilized in the preparation of the catalyst or in the preparation of PVC therewith. While this patent broadly encompasses certain alkylmagnesium alkoxides and certain magnesium dialkoxides, it has nothing to do with any concept or objective of producing certain magnesium dialkoxides which have materially enhanced solubility in hydrocarbon or chlorinated hydrocarbon solvents. Indeed, most of the catalysts of said patent are alkyl aluminum alkoxides or aluminum alkoxides, and some others are LiOBu and the aforementioned $(C_4H_9)Mg(OC_3H_7)$.

Towers (U.S. Pat. No. 3,094,546) deals with processes for preparing, among other compounds, metal alkoxide compounds. Among such alkoxide compounds are magnesium methylate. Towers does not remotely deal with the production of magnesium dialkoxides in hydrocarbon or chlorinated hydrocarbon solvents, let alone any solution to the problem of producing particular types of magnesium dialkoxides having excellent solubility in hydrocarbon or chlorinated hydrocarbon solvents made in accordance with certain facets of the present invention.

It has also heretofore been known, as disclosed in European Patent Application (EPO) Publication No. 0 156 512 Al, to produce certain olefin polymerization titanium-containing catalysts by contacting an inert solvent (e.g., a hydrocarbon solvent)-soluble magnesium alkoxide with certain silicon compounds and an electron donor compound, the magnesium dialkoxides used in the preparation of said catalysts being represented by the formula $Mg(OR)(OR^1)$, where R and $R^1$ are the same or different alkyl, cycloalkyl, aryl, alkenyl, or aralkyl groups. It is pointed out in said EPO publication that those magnesium dialkoxides having hydrocarbon groups with less than 7 carbon atoms are insoluble in inert solvents, such as hydrocarbon and chlorinated hydrocarbon solvents, and that it is, therefore, necessary that the hydrocarbon groups in the magnesium dialkoxides, used in the preparation of the aforementioned catalysts of this EPO Publication, should have a carbon number greater than 7 and side chains. Numerous examples of magnesium dialkoxides which contain a carbon number greater than 7 and which are stated to be useful in the preparation of said catalysts are given, illustrative of which are magnesium di-2-ethylhexyloxide, magnesium di-2-methylhexyloxide, magnesium di-2-(methylethyl) pentyloxide; and, also, such magnesium dialkoxides as magnesium di-1-ethylhexyloxide, magnesium di-1-ethylpentyloxide, magnesium di-1-propylbutoxide, magnesium di-1-methylheptyloxide, magnesium di-4-methylcyclohexyloxide, and many others. Methods of preparation of said magnesium dialkoxides are also disclosed as, for instance, by reacting metallic magnesium or dihydrocarbyl magnesium with an alcohol represented by ROH or R′OH (where R and R′ are the same as defined above); or, alternatively, by reacting a magnesium dialkoxide insoluble in an inert solvent with an alcohol having the same hydrocarbon group as the desired dialkoxide has.

With due regard for what has been noted above is stated in said EPO Publication with respect to the preparation and the manner of preparation of magnesium dialkoxides which are soluble in the aforementioned hydrocarbon or chlorinated hydrocarbon solvents, so far as I have been able to ascertain, based upon much experimental work, linear, unbranched secondary magnesium dialkoxides do not, in fact, generally speaking, form flowable, and particularly relatively readily flowable, clear solutions in hydrocarbon or chlorinated hydrocarbon solvents unless there is present in the preparation thereof, or added, aluminum compounds such as, by way of example, aluminum trialkyls exemplified by triethyl aluminum and triisobutyl aluminum; or aluminum trialkoxides exemplified by aluminum triethoxide and aluminum triisopropoxide. In other words, in the absence of such or other aluminum compounds, the magnesium dialkoxides, or purported magnesium dialkoxide compositions, are obtained in forms which are generally highly objectionable intractable solids or semi-solid gel-like compositions.

Thus, in connection with the foregoing, reference is first made to Example 1 on Page 15 of the aforesaid EPO Publication where the preparation of a colorless transparent viscous solution of the magnesium dialkoxide, specifically, magnesium di-2-ethylhexyloxide, is described. In the preparation of said magnesium dialkoxide, briefly summarized, to a solution of butylethyl magnesium in n-heptane (which butylethyl magnesium is a commercially produced composition designated as MAGALA BEM, a product of Texas Alkyls Co., Ltd. in U.S.) there is added, dropwise, a mixture of 2-ethylhexanol and n-heptane, with stirring, and then the resulting mixture is heated to 120° C. and stirred at the reflux temperature of n-heptane for 1 hour to complete the reaction. It is well-known to those familiar with the art that BEM (which is an abbreviation for butylethyl magnesium), for which Texas Alkyls Co. issues a product data sheet in the U.S., which clearly shows the presence of 0.02 to 0.05 wt. % aluminum in product solutions containing 2.1 to 2.3 wt. % magnesium (the latter figure corresponding to 10 wt. % of BEM). A laboratory analytical report put out by Texas Alkyls Co. accompanying a pint bottle of the MALAGA BEM shows the presence of 0.05 wt. % of aluminum and 2.20 wt. % magnesium in the solution. It is clear, therefore, that, in Example 1 of said EPO Publication, the magnesium dialkoxide contained aluminum, and, to those skilled in the art, in the form of an organoaluminum compound. In this regard, it may additionally be pointed out that it is also generally known to the art that the addition of various organoaluminum compounds, such as trialkylaluminum compounds, to linear (unbranched) di-alkylmagnesium compounds such as, for example, n-butyethylmagnesium, di-n-hexylmagnesium, and di-n-butylmagnesium promotes or enhances the solubility of these dialkylmagnesium compounds in hydrocarbon or chlorinated hydrocarbon solvents and lowers the viscosity of such solutions sufficiently to allow them to be easily handled (as, for instance, by pumping) as shown, by way of illustration, in U.S. Pat. No. 3,737,393.

The foregoing situation, in relation to Example 1 of said EPO Publication, has the same applicability to Examples 10 to 12 of said EPO Publication, where the MAGALA BEM is shown to have been used in the preparation of magnesium dialkoxide heptane solutions of magnesium di-1-methylhexyloxide, magnesium di-1-methylheptyloxide, and magnesium di-1-dimethylpentyloxide (linear, unbranched secondary magnesium dialkoxides), that is, they contain aluminum compounds.

Experimental work conducted by me and/or under my direction using, in place of MAGALA BEM, dibutyl magnesium (DBM), specifically n-butyl-sec-butyl magnesium, a partially branched dialkylmagnesium) solutions in heptane, or other hydrocarbon or chlorinated hydrocarbon solvents, prepared by me or other chemists employed by the Assignee of the present application, and containing no aluminum compounds, when reacted with 2-heptanol to produce magnesium di-1-methylheptyloxide, resulted in the formation of an intractable solid gel. The said gel was able to be brought into solution by the addition of triisobutylaluminum plus some additional 2-heptanol or 2-octanol. This experiment was repeated with other linear, unbranched $C_5$–$C_{10}$ secondary magnesium dialkoxides, such as magnesium di-1-ethylpentyloxide (magnesium bis-3-heptyloxide), magnesium di-1-ethylhexyloxide (magnesium bis-3-octyloxide), magnesium di-1-methylnonyloxide (magnesium bis-2-decyloxide), and magnesium di-1-n-propylheptyloxide (magnesium bis-4-decyloxide). In all cases, intractable solid gels were obtained in the absence of aluminum trialkoxides as generated by (a) addition of trialkylaluminum compounds to the precursor DBM prior to reaction with the corresponding alcohol or (b) by addition of trialkylaluminum compounds to the formed gels followed by additional corresponding alcohol.

With further regard to the aforesaid EPO Publication, in those Examples thereof for the preparation of magnesium dialkoxide solutions wherein no organolaluminum compounds are employed, namely Examples 2 and 3 (magnesium di-2-ethylhexyloxide), viscous solutions low in magnesium concentration (0.1–0.3 M) are produced. (These are examples of branched primary magnesium dialkoxides, rather than the unbranched secondary dialkoxides discussed above.) Such viscous, low concentration solutions have the twin disadvantages of being difficult to pump from one container to another and of requiring the uneconomical shipment of large quantities of solvent relative to the contained product therein.

It is in order to note that in appreciable numbers of cases, especially in the use of magnesium dialkoxide solutions to prepare catalysts for the polymerization of olefins, it is advantageous to have little or preferably no aluminum alkoxide present in the magnesium dialkoxide solutions used to generate the magnesium chloride carrier for the titanium-bearing polyolefin catalyst, as the resulting magnesium chloride crystallites are contaminated with aluminum chloride. On subsequent treatment of the resulting catalyst with aluminum alkyl co-catalyst, the occluded aluminum chloride can be leached out, thus causing degradation of the MgCl$_2$ crystal lattice, leading to undesirable changes in the selectivity of the catalyst, and in some cases to a lower catalyst efficiency.

In order to demonstrate the facts in the relation to the absence of organoaluminum compounds on the nature of the magnesium dialkoxide compositions of the type made according to such Examples as 1 and 10 to 12 of the aforementioned EPO Publication, there is set forth below the results of some illustrative experiments which were carried out by me and/or under my direction:

Comparative Similar Examples of EPO Publication 156 512 A 1 which did not give fluid solutions of magnesium dialkoxides with DBM (n butyl-sec-butylmagnesium - no Al initially present)

Ia. Magnesium Di-1-Methylnonyloxide (Magnesium Bis-2-Decyloxide) - Theory Conc.=0.87 M Mg 5.49 g (34.68 mmoles) of 2-decanol dissolved in 5 ml of methylcylcohexane was added dropwise to 7.62 g of a 1.0 molar solution of n-butyl-sec-butylmagnesium (17.34 mmoles) in heptane with constant shaking. A gel formed, but which dissolved on addition of 1 ml of a 0.89 molar solution of tri-n-butylaluminum in heptane at the halfway point in the addition of the 2-decanol solution.

IIa. Magnesium Di-1-n-Propylheptyloxide (Magnesium Bis-4-Decyloxide) - Theory Conc.=0.68 M 4.82 g (30.45 mmoles) of 4-decanol, dissolved in 8 ml of methylcyclohexane, was added dropwise to 6.69 g (15.24 mmoles) of a 1.0 molar solution of n-butyl-sec-butylmagnesium in heptane with constant shaking. A heavy, clear, rubbery gel formed after the halfway point in the addition of the 4-decanol solution with no free liquid present. No aluminum trialkyl was present.

IIIa. Magnesium Di-1-Ethylhexyloxide (Mg-Bis-3-Octyloxide - Theory Conc.=1 M Mg 10 ml of a 2 molar solution of n-butyl-sec-butylmagnesium in chlorobenzene was added dropwise to a solution of 3-octanol (5.73 g, 0.044 moles) dissolved in 5 ml of chlorobenzene. A clear, glass gel was obtained after half of the dibutylmagnesium solution was added. Dilution with an additional 5 ml of chlorobenzene did not help to break up the gel. The remainder of the dibutylmagnesium solution was not added.

IVa. Magnesium Di-1-Methylheptyloxide (Mg-Bis-2-Octyloxide) - Theory Conc.=0.75 M Mg To 10 ml of a 1.5 molar solution of n-butyl-sec-butylmagnesium in heptane was added dropwise (with cooling) 10 ml of a solution of 4.8 ml (3.9 g, 30 mmoles) of 2-octanol in heptane. The reaction mixture began to thicken at the halfway point in the addition, becoming quite viscous. As the alcohol addition proceeded further, the reaction mix became gelatinous, and a solid mass resulted. Addition of 5 ml of 0.9 molar triisobutylaluminum in hexane (in 1 ml increments) along with about 1 ml of 2-octanol, followed by vigorous shaking, eventually broke up most of the solid mass and led to a fluid solution. This amount of triisobutylaluminum corresponds to 30 mole % aluminum alkoxide based on magnesium dialkoxide present.

Va. Magnesium Di-1-Ethylpentyloxide (Mg-Bis-3-Heptyloxide) - Theory Conc.=0.75 M 3.5 g (4.3 ml, 30 mmoles) of 3-heptanol (racemic) in 10 ml of heptane solution was added dropwise, with cooling and shaking, to 10 ml of a 1.5 molar solution of n-butyl-sec-butylmagnesium in heptane. The mixture gradually thickened to an intractable gel as addition of the alcohol proceeded beyond 50%, with the final 20% requiring mixing of the reaction mass with a spatula.

VIa. Magnesium Di-1-Methylbutoxide (Mg-Bis-2-Pentyloxide) - Theory Conc.=0.75 M

To 10 ml of a 1.5 molar solution of n-butyl-sec-butylmagnesium in heptane was added dropwise, with cooling and shaking, 10 ml of a solution of 3.26 ml (2.65 g, 30 mmoles) of 2-pentanol in heptane. A solid gel resulted, which, however, reformed into a flowable solution by addition of 5 ml of a 0.9 Molar solution of triisobutylaluminum in hexane, followed by 0.5 ml of 2-pentanol. The Mg concentration of this final solution was 0.6 Molar.

SUMARY OF THE INVENTION

In accordance with certain aspects of the practice of my present invention, alcohols of the type described below are reacted with magnesium dialkyls, or magnesium metal, or alkyl magnesium alkoxides, in liquid aliphatic or aromatic hydrocarbon or chlorinated hydrocarbon solvent media, with no organoaluminum compounds being present, to form highly soluble, stable solutions of novel and highly useful magnesium dialkoxide- or magnesium dialkoxide-containing compositions.

Whereas $C_1$–$C_{18}$ magnesium secondary and tertiary dialkoxides lacking alkyl substituents on those carbon atoms not directly bearing the oxymagnesium moiety, generally speaking, have a low order of solubility (less than about 0.4 molar) in liquid hydrocarbon or chlorinated hydrocarbon solvents, I have found that certain aliphatic or cycloaliphatic or acyclic $C_5$–$C_{18}$ magnesium dialkoxides namely, those which possess alkyl, most advantageously $C_1$–$C_4$ alkyl, substituents on carbon atoms beta ($\beta$) and/or gamma ($\gamma$) to the carbon atoms bearing the oxymagnesium moiety generally have a particularly high order of solubility in such solvents (generally about 0.7 molar and above). In other words, I have made, among other discoveries, which I consider unexpected, in view of prior knowledge and teachings which have heretofore been known to the art, that one or more of the foregoing disadvantages of formation of intractable gels, high viscosity, low concentration and aluminum content in methods of preparation of magnesium dialkoxide solutions, and in the resulting magnesium dialkoxide solutions can be avoided by the use of certain novel secondary and tertiary magnesium dialkoxides, particularly possessing $C_1$–$C_4$ alkyl branches attached at positions along the main carbon chain beta or gamma relative to the carbon-bearing oxygen of said magnesium dialkoxide. The resulting novel magnesium dialkoxides generally possess a high solubility (1 M) in hydrocarbon or chlorinated hydrocarbon solvents, as well as a high mobility (fluidity) in these solvents in the absence of any aluminum compounds whatsoever. This difference can be represented illustratively by the following pairs of structures:

Secondary Magnesium Dialkoxides

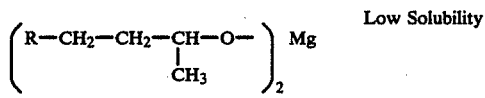
Low Solubility

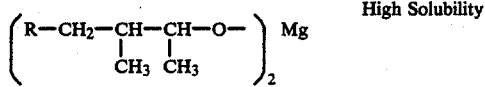
High Solubility

Tertiary Magnesium Dialkoxides

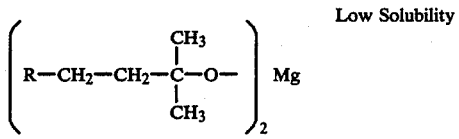
Low Solubility

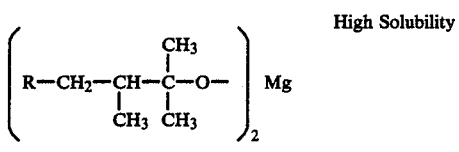
High Solubility

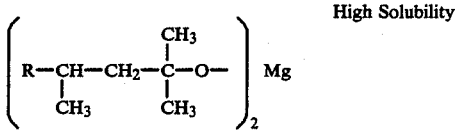
High Solubility

In the foregoing formulae, R is the balance of the secondary and tertiary monohydric alcohols of the particular types used in producing the secondary and tertiary dialkoxides such as are made in accordance with the present invention.

In the following Table, there are disclosed illustrative magnesium dialkoxides prepared in accordance with the present invention and their highly desirable properties from the standpoints of their excellent solubilities and nature of the solutions. They are effectively prepared, in accordance with the present invention, by reacting, most desirably in a liquid hydrocarbon or chlorinated liquid hydrocarbon media, aliphatic or cycloaliphatic or acylic $C_5$–$C_{18}$ beta or gamma alkyl-substituted secondary or tertiary monohydric alcohols with suspensions of metallic magnesium or magnesium amide or dialkylmagnesium compounds in the absence of trialkylaluminums or aluminum trialkoxides.

TABLE 1

| Magnesium Dialkoxide | Type of Alkyl Substitution | Solvent Type | Conc. (M) | Physical Description of Reaction Mixture |
|---|---|---|---|---|
| 2,6-Dimethyl-4-heptyloxide | Gamma | Chlorobenzene | 0.89 | Clear fluid solution at 55° |
| 2,3-Dimethyl-3-pentyloxide | Beta | Heptane | 0.93 | Clear fluid solution at 25° |
| 3,5-Dimethyl-3-hexyloxide | Gamma | Heptane | 0.97 | Clear fluid solution at 25° |
| 2,3-Dimethyl-2-pentyloxide | Beta | Heptane | 1.03 | Clear fluid solution at 25° |
| 2-tert-Butyl-cyclohexyloxide | Beta | Heptane | 0.88 | Clear fluid solution at 25° |
| 2,6,8-Trimethyl-4-nonyloxide | Gamma | Heptane | 0.90 | Clear fluid solution at 25° |
| 2,2-Dimethyl-3-heptyloxide | Beta | Heptane | 0.75 | Clear fluid solution at 25° |
| 2,4-Dimethyl-3-hexyloxide | Beta | Heptane | 0.75 | Clear fluid solution at 25° |
| 3,5-Dimethyl-4-heptyloxide | Beta | Heptane | 0.75 | Clear fluid solution at 25° |
| 2,2-Dimethyl-3-hexyloxide | Beta | Heptane | 0.75 | Clear fluid solution at 25° |
| 4-Ethyl-3-hexyloxide | Beta | Heptane | 0.75 | Clear fluid solution at 25° |
| 2,6-Dimethyl-cyclohexyloxide | Beta | Heptane | 0.60 | Clear fluid solution at 25° |
| 3-Methyl-4-Octyloxide | Beta | Heptane | 0.75 | Clear fluid solution at 25° |
| 2,4-Dimethyl-3-pentyloxide | Beta | Methylcyclohexane | 1.59 | Clear fluid solution at 25° |
| 2,3-Dimethyl-2-hexyloxide | Beta | Cyclohexane | 0.67 | Clear fluid solution at 25° |

The foregoing magnesium dialkoxides, as to the nature of their chemical structure, are shown illustratively below:

| Magnesium Dialkoxide | Molecular Formula |
|---|---|
| 2,6-Dimethyl-4-heptyloxide | 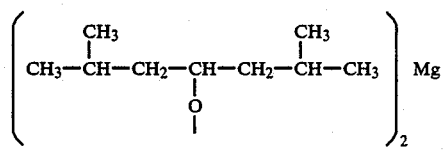 |
| 2,3-Dimethyl-3-pentyloxide | 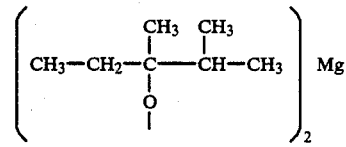 |

-continued

| Magnesium Dialkoxide | Molecular Formula |
|---|---|
| 3,5-Dimethyl-3-hexyloxide | $\left[ \begin{array}{c} \text{CH}_3\text{—CH(CH}_3\text{)—CH}_2\text{—C(CH}_3\text{)(O)—CH}_2\text{—CH}_3 \end{array} \right]_2 \text{Mg}$ |
| 2,3-Dimethyl-2-pentyloxide | $\left[ \text{CH}_3\text{—CH}_2\text{—CH(CH}_3\text{)—C(CH}_3\text{)(O)—CH}_3 \right]_2 \text{Mg}$ |
| 2-tert-Butylcyclohexyloxide | $\left[ \text{2-tert-butylcyclohexyl-O—} \right]_2 \text{Mg}$ |
| 2,6,8-Trimethyl-4-nonyloxide | $\left[ \text{CH}_3\text{—CH(CH}_3\text{)—CH}_2\text{—CH(CH}_3\text{)—CH}_2\text{—CH(O)—CH}_2\text{—CH(CH}_3\text{)—CH}_3 \right]_2 \text{Mg}$ |
| 2,2-Dimethyl-3-heptyloxide | $\left[ \text{CH}_3\text{—CH}_2\text{—CH}_2\text{—CH}_2\text{—CH(O)—C(CH}_3\text{)}_3 \right]_2 \text{Mg}$ |
| 2,4-Dimethyl-3-hexyloxide | $\left[ \text{CH}_3\text{—CH}_2\text{—CH(CH}_3\text{)—CH(O)—CH(CH}_3\text{)—CH}_3 \right]_2 \text{Mg}$ |
| 3,5-Dimethyl-4-heptyloxide | $\left[ \text{CH}_3\text{—CH}_2\text{—CH(CH}_3\text{)—CH(O)—CH(CH}_3\text{)—CH}_2\text{—CH}_3 \right]_2 \text{Mg}$ |
| 4-Ethyl-3-hexyloxide | $\left[ \text{CH}_3\text{—CH}_2\text{—CH(CH}_2\text{CH}_3\text{)—CH(O)—CH}_2\text{—CH}_3 \right]_2 \text{Mg}$ |
| 2,6-Dimethylcyclohexyloxide | $\left[ \text{2,6-dimethylcyclohexyl-O—} \right]_2 \text{Mg}$ |

-continued

| Magnesium Dialkoxide | Molecular Formula |
|---|---|
| 3-Methyl-4-octyloxide | $\left( CH_3-CH_2-CH_2-CH_2-CH(O-)-CH(CH_3)-CH_2-CH_3 \right)_2 Mg$ |
| 3,5-Dimethyl-4-heptyloxide | $\left( CH_3-CH(CH_3)-CH(O-)-CH(CH_3)-CH_3-CH_3 \right)_2 Mg$ |
| 2,4-Dimethyl-3-pentyloxide | $\left( CH_3-CH(CH_3)-CH(O-)-CH(CH_3)-CH_3 \right)_2 Mg$ |
| 2,3-Dimethyl-2-hexyloxide | $\left( CH_3-CH_2-CH_2-CH(CH_3)-C(CH_3)(O-)-CH_3 \right)_2 Mg$ |

In one illustrative process of the practice of the invention, a dialkylmagnesium dissolved in a liquid hydrocarbon solvent is reacted with slightly more than twice the molar equivalent, based on magnesium, of the aforesaid aliphatic or cycloaliphatic $C_5$-$C_{18}$ beta- or gamma-alkyl-substituted secondary or tertiary monohydric alcohols, or a mixture of said alcohols, either neat or generally more advantageously in solution in a liquid hydrocarbon or chlorinated hydrocarbon solvent. Alkanes are generally rapidly generated and can be driven off by heating to the boiling point if low boiling (ca 0°–5° C.), or absorbed by the solution itself.

In place of a part of the aliphatic or cycloaliphatic or acyclic $C_5$-$C_{18}$ beta- or gamma-alkyl-substituted secondary or tertiary monohydric alcohols, various secondary or tertiary alcohols can be used, such as isopropanol or sec-butanol or tert-butanol most favorably up to about a 1:1 molar ratio, based on said aliphatic or cycloaliphatic or acyclic $C_5$-$C_{18}$ beta-or gamma-alkyl-substituted secondary or tertiary monohydric alcohol or mixtures of such alcohols, although somewhat more can be employed. Also contemplated are beta-alkyl-substituted primary monohydric alcohols, such as 2-methylpentanol and 2-ethylhexanol in admixture with the alcohols utilized in the practice of this invention, as well as primary linear (unsubstituted) alcohols such as n-butanol and n-octanol.

The excess of $C_5$-$C_{18}$ beta- or gamma-alkyl-substituted secondary or tertiary monohydric alcohol employed over and above twice the molar equivalent (based on magnesium) is generally in the range of about 0.01 to about 2.0 molar equivalents, based on magnesium, but more advantageously lies in the range of about 0.1–1.0 molar equivalents. This addition of an excess of the $C_5$-$C_{18}$ beta- or gamma-alkyl-substituted secondary or tertiary monohydric alcohols is, generally, not necessary, but it has the advantage of driving the reaction to completion.

Although, according to my present invention, as I have described and shown above, said $C_5$-$C_{18}$ beta- or gamma-alkyl-substituted secondary or tertiary monohydric alcohols, on reaction with dialkylmagnesium compounds, generally do not require the presence of of a trialkylaluminum, or of an added aluminum trialkoxide, or other organoaluminum compound, to effect solubility, it has been found by me that the presence of these organoaluminum compounds can be employed to yield hydrocarbon or chlorinated hydrocarbon solvent-soluble magnesium dialkoxides alone or when utilizing, in part, other alcohols.

Gessell (see above) teaches the use, in his catalyst preparations, of major amounts of aluminum trialkoxides to promote the solubility of magnesium dialkoxides in liquid hydrocarbon or chlorinated hydrocarbon solvents. This is substantiated by the use of at least 50 mole % of aluminum (based on magnesium) and the sole use of n-propanol in the magnesium dialkoxide preparative examples shown in his patents. In essence, Gessell discloses the preparation of liquid hydrocarbon-soluble magnesium dialkoxide-aluminum trialkoxide complexes, rather than the liquid hydrocarbon or chlorinated hydrocarbon solvent-soluble novel magnesium dialkoxides constituting one of the important aspects of the present invention. In the preparation of some alpha-olefin $MgCl_2$-based catalyst supports, it is beneficial to have little or no aluminum in the $MgCl_2$ precursor compound. Thus, the present invention provides novel and useful products for such application.

The contrast between the nature and advantages as to the achievement of good to excellent solubilities of the novel magnesium dialkoxide compounds of my invention may be contrasted with the results achieved in certain illustrative examples when the present invention is not practiced. Thus, certain aliphatic or cycloaliphatic or acyclic $C_3$–$C_{18}$ non-beta- and/or gamma-alkyl-substituted secondary or tertiary monohydric alcohols, on reaction with dialkylmagnesium compounds, form magnesium dialkoxides of a low order of solubility in hydrocarbon and chlorinated hydrocarbon solvents, even in the presence of substantial amounts of aluminum trialkoxides as shown below in Table 2.

TABLE 2

| Magnesium Dialkoxide | Solvent Type | Conc. (M) | Physical Description of Reaction Mixture |
|---|---|---|---|
| Isopropoxide | Heptane-Cyclohexane or Toluene | | Solid gel |
| sec-Butoxide | Heptane-Cyclohexane | 0.38 | Fluid slurry of fine particles |
| 3-Heptyloxide (Magnesium di-1-ethyl-pentyloxide)* | Heptane | | Solid gel |
| 3-Octyloxide (Magnesium di-1-ethyl-hexyloxide)* | Chlorobenzene | | Solid gel |
| 2-Octyloxide (Magnesium di-1-methyl-heptyloxide)* | Heptane | | Solid gel (a) |
| 2-Decyloxide (Magnesium di-1-methyl-nonyloxide)* | Methylcyclohexane/heptane | | Solid gel (b) |
| 4-Decyloxide (Magnesium di-1-n-propyl-heptyloxide)* | Methylcyclohexane/Heptane | | Solid gel |
| tert-Butoxide | Cyclohexane | | Thick slurry forms which sets to solid mass on standing |
| 3-Methyl-3-Pentyloxide | Heptane-Cyclohexane or Toluene | 0.26 | Solid slurry |
| tert-Amyloxide | Heptane-Cyclohexane | 0.38 | Solid slurry |

*Alternative compound terminology
(a) Gel dissolves slowly on addition of 30 mole % of an aluminum trialkoxide.
(b) Gel dissolves on addition of 5 mole % of an aluminum trialkoxide.

In contrast to these results, as described above, I have found that the above-disclosed aliphatic or cycloaliphatic or acyclic $C_5$–$C_{18}$ beta- or gamma-alkyl-substituted secondary or tertiary monohydric alcohols on reaction, for instance, with dialkylmagnesium compounds, even in the absence of aluminum trialkoxides or an excess of the alcohol of reaction, form magnesium dialkoxides with a significantly improved high or relatively high order of solubility in hydrocarbon or chlorinated hydrocarbon solvents.

Additionally, the hydrocarbon and chlorinated hydrocarbon solvent-soluble magnesium dialkoxides [Mg(OR)$_2$] of the present invention can be readily mixed with hydrocarbon and chlorinated hydrocarbon solvent-soluble magnesium dialkyls (R$_2$Mg) to form soluble alkylmagnesium alkoxides (R'MgOR) which have utility in the preparation of halogen-free Ziegler catalysts which catalyze the polymerization of olefins, diolefins, or olefin oxides. Such a procedure for forming alkylmagnesium alkoxides is superior to that described in either Malpass (U.S. Pat. No. 4,133,824) or Mueller (U.S. Pat. No. 4,410,742 to Schering A.G.) in that no insoluble magnesium dialkoxide need be employed which would tend to slow the reaction with dialkylmagnesium compounds or incompletely react therewith. In addition, ratios of Mg(OR)$_2$ to MgR'$_2$ may be significantly higher than 1.0 without causing a loss of product from solution by precipitation, as would occur in the Malpass or Mueller inventions. Integral ratios are also unnecessary, values of the alkoxide (OR) to alkyl (R') ratios being continuously variable from about 9:1 to about 1:9.

Other alcohols which advantageously can be admixed with the above aliphatic or cycloaliphatic or acyclic $C_5$–$C_{18}$ beta- or gamma-alkyl-substituted secondary and/or tertiary monohydric alcohols and co-reacted with dialkylmagnesium compounds, as noted above, are $C_3$–$C_{18}$ aliphatic beta- or gamma-alkyl-unsubstituted secondary or tertiary alcohols, such as isopropanol, sec-butanol, 2-pentanol, tert-butanol, tert-amyl alcohol, 3-methyl-3-pentanol, and the like, as well as $C_1$–$C_{18}$ aliphatic primary (linear, unsubstituted) alcohols, such as methanol, ethanol, n-butanol, n-hexanol, n-octanol, and aliphatic primary 2-alkyl-substituted alcohols, such as 2-methyl-pentanol and 2-ethylhexanol, and the like. The amounts of said alcohols which can be co-reacted with said aliphatic or cycloaliphatic or acyclic $C_5$–$C_{18}$ beta- or gamma-alkyl-substituted alcohols can be varied from about 0.1 to about 2 moles per mole of said $C_5$–$C_{18}$ beta- or gamma-alkyl-substituted alcohols, but are preferably in the range of about 0.5 to about 1 mole per mole of said alcohol, and most favorably in the range of 0.7 to 1 mole per mole of said alcohol.

Aliphatic or cycloaliphatic or acyclic $C_5$–$C_{18}$ beta- and/or gamma-alkyl-substituted secondary alcohols, i.e., those of said secondary alcohols bearing at least one $C_1$–$C_4$ alkyl branch at the carbon atom beta and/or gamma to the hydroxyl group which are reacted with magnesium metal or with magnesium amide or with dialkylmagnesium compounds, optionally in the presence of small quantities (2–5 mole % of Mg) of trialkylaluminums or aluminum alkoxides in various embodiments of the present invention, are exemplified by 2-methyl-3-pentanol; 2,2-dimethyl-3-pentanol; 2,4-dimethyl-3-pentanol; 3-methyl-2-pentanol; 3-methyl-2-butanol; 4-methyl-3-hexanol; 3-methyl-2-hexanol; 2,4-dimethyl-3-hexanol; 3,4-dimethyl-2-hexanol; 2,4-dimethyl-3-heptanol; 4-methyl-3-heptanol; 2-methyl-3-octanol; 2,2-dimethyl-3-octanol, and the like. Also contemplated are beta-alkyl-substituted cyclic $C_6$–$C_{18}$ secondary and/or tertiary alcohols, such as 2-methylcyclopentanol; 2-methylcyclohexanol; 2,6-dimethylcyclohexanol; 2-tert-butylcyclohexanol; and the like. Most preferred are those cyclic secondary or tertiary alcohols bearing at least two beta or gamma methyl groups or one beta-sec- or tert-butyl group relative to the hydroxyl moiety.

Beta- or gamma-alkyl-substituted $C_6$–$C_{18}$ cyclic or acyclic tertiary alcohols, i.e., those tertiary alcohols bearing at least one $C_1$–$C_4$ alkyl branch at the carbon atom beta or gamma to the hydroxyl group which are reacted with magnesium metal or with magnesium amide or dialkylmagnesium compounds, optionally in the presence of small quantities (2 to 5 mole % of Mg) of aluminum alkoxides, in various embodiments of the invention, are exemplifed by 2,3-dimethyl-2-butanol; 2,3-dimethyl-2-pentanol; 2,3-dimethyl-3-pentanol; 2,3-dimethyl-2-hexanol; 3,4-dimethyl-4-heptanol; 2,3,4-trimethyl-3-pentanol; 3,4,4-trimethyl-3-hexanol; 1,2-dimethylcyclopentanol; 1,2,6-trimethylcyclohexanol, and the like.

Other less preferably $C_6-C_{18}$ secondary and tertiary cyclic and acyclic alcohols which are reacted with magnesium metal or magnesium amide or with dialkylmagnesium compounds, optionally in the presence of small amounts of aluminum trialkyls or aluminum trialkoxides in a further embodiment of my invention, are those alcohols bearing alkyl group substitution further than the beta position from the carbon atom bearing the hydroxyl group, namely, on the gamma carbons. Examples of such alcohols are 4-methyl-2-pentanol; 5-methyl-3-hexanol; 2,6-dimethyl-4-heptanol; 2-methyl-4-octanol; 3,5-dimethyl-3-hexanol; 2,6,8-trimethyl-4-nonanol; and 3-methylcyclohexanol. A general rule to be followed is that the longer the main chain of carbon atoms in the alcohol and the greater the number of substituent alkyl groups, the greater the solubility of the resulting magnesium dialkoxides under the same conditions. Thus, 2,6,8-trimethyl-4-nonanol gives a magnesium dialkoxide which is highly soluble in heptane at room temperature, whereas, for instance, 2,6-dimethyl-4-heptanol produces a soluble magnesium dialkoxide in chlorobenzene (a more polar solvent than heptane), and then only above 50° C.

As noted above, mixtures of a variety of the foregoing referred to alcohols with each other is also contemplated, as well as admixture of these with those beta- or gamma-alkyl-unsubstituted secondary and tertiary alcohols and other alcohols for admixture with the aliphatic, cycloaliphatic or acyclic $C_5-C_{18}$ beta- and/or gamma-alkyl-substituted aliphatic monohydric alcohols.

Advantageously, as indicated generally above, an excess of the alcohol or mixture of alcohols, above that necessary to react with all of the dialkymagnesium present, may be employed in order to drive the reaction to completion. This excess of alcohol can vary, as noted previously. The said alcohols can be added to the dialkylmagnesium compounds in either neat form or dissolved in a liquid hydrocarbon and chlorinated hydrocarbon solvent of choice.

The dialkylmagnesium compounds employed in the reaction with the above alcohols can be varied widely. For convenience, they are generally soluble in liquid hydrocarbon and chlorinated hydrocarbon media, although it is not outside the scope of the present invention to employ dialkylmagnesium compounds or diarylmagnesium compounds which are, as such, insoluble in liquid hydrocarbon and chlorinated hydrocarbon media. Included are typical dialkylmagnesiums, such as n-butyl-sec-butylmagnesium; n-butyl-ethylmagnesium; di-n-hexylmagnesium; di-isopropyl-magnesium; di-n-butylmagnesium; di-sec-butylmagnesium; di-2-methylbutylmagnesium; di-n-amylmagnesium; n-butyl-n-octylmagnesium; ethyl-isoamylmagnesium; and typical diarylmagnesium compounds, such as diphenylmagnesium; di-o-tolylmagnesium, and the like.

It is also within the scope of my present invention to react the aforesaid aliphatic, cycloaliphatic or acyclic $C_5-C_{18}$ beta- and/or gamma-alkyl-substituted secondary and tertiary monohydric alcohols used in accordance with the invention with magnesium metal or magnesium compounds other than dialkylmagnesiums. For example, and as noted above, magnesium amide, $Mg(NH_2)_2$, can be reacted with said alcohols in a liquid hydrocarbon medium in a manner similar to that described for the production of certain calcium or barium and strontium alkoxides from calcium or barium metals or amides, as described in my U.S. Pat. No. 4,555,498, dated Nov. 26, 1985. Other methods include reaction of the above-described particular types of alcohols with magnesium metal or magnesium hydride, transalcoholysis of lower $C_1-C_3$ magnesium alkoxides with said alcohols, or reaction of the alkali metal alkoxide derivatives of said alcohols with magnesium halide salts. However, for optional economy in the production of the novel resulting magnesium dialkoxides of the present invention, the lowest-price magnesium compounds, coupled with the simplest process parameters, are most advantageous.

The reaction of the aforementioned alcohols, used in accordance with the present invention, with the dialkylmagnesium compounds can be carried out at any convenient temperature. Generally, it is preferred to carry out the reaction at lower ranges of temperatures, i.e., below the boiling point of the liquid hydrocarbon and chlorinated hydrocarbon solvent employed. The said alcohols can be added to the dialkylmagnesium compounds, or vice versa. Addition is generally carried out incrementally.

Although, as I have described above, it is the particularly important aspect of my present invention to produce magnesium dialkoxide solutions having a relatively high order of solubility, and being readily flowable, in organic solvents, most desirably hydrocarbon or chlorinated hydrocarbon solvents, in which aliphatic or cycloaliphatic or acyclic $C_5-C_{18}$ magnesium dialkoxides, namely, those which possess $C_1-C_4$ alkyl substituents on carbon atoms ($\beta$) and/or gamma ($\gamma$) to the carbon atoms bearing the oxymagnesium moiety without the presence or use of organoaluminum compounds, it is not to be understood that the novel magnesium alkoxide solutions of my present invention are required to be free of organoaluminum compounds. In those instances in which organoaluminum compounds are not contra-indicated for any particular use of the magnesium dialkoxide solutions, they may be incorporated into said magnesium dialkoxide solutions in varying proportions, small or large, as the case may be as indicated to obtain certain effects. Thus, for instance, it may, in certain cases, be desirable to enhance even greater the solubility of the magnesium dialkoxides in the magnesium dialkoxide solutions made with no organoaluminum compounds present, or to decrease even further the viscosities of such solutions by adding thereto organoaluminum compounds. The amounts of any such added organoaluminum compounds can, for example, be as low, as to produce in the solutions of the magnesium dialkoxides, as 0.01 to 0.05 wt. %, calculated as metallic aluminum, where said solutions contain, for example from about 2 to about 2.5 wt. % of magnesium based on the amount or content of the magnesium dialkoxide in the solution. The amount of such added organoaluminum compounds, advantageously trialkylaluminum or aluminum trialkoxide compounds, which can be added will, generally speaking, vary from about 0.01 to about 5 or 10 moles per mole of magnesium dialkoxide, and most advantageously in the range of about 0.05 to about 2 moles of said organoaluminum compounds per mole of dialkylmagnesium compound. Typical of the trialkylaluminum compounds employable are triethylaluminum; triisobutylaluminum; tri-n-butylaluminum; tri-n-hexylaluminum; diethyl-n-butylaluminum; tri-n-octylaluminum; and the like. Typical aluminum trialkoxide compounds employable are aluminum triisopropoxide; aluminum tri-n-butoxide; aluminum tri-2-methylpentyloxide; aluminum tricyclohexyloxide; and the like. Such complexes, for instance, can be used in the production of catalyst systems for the polymerization of olefins.

In place of or in addition to the trialkylaluminum or aluminum trialkoxide compounds mentioned above which may be added to the dialkylmagnesium compounds after reaction with the aforesaid types of alcohols, there can be added other organometallic compounds or metallic alkoxides, such as boron trialkoxides, dialkylzincs, alkyllithiums, alkylsodiums, potassium alkoxides, sodium alkoxides, zinc dialkoxides, and the like. Generally, amounts of added organometallic compound, metallic alkoxide, or other metal derivative can be varied in the range specified above for the trialkylaluminums or the aluminum trialkoxides per mole of magnesium compound. Typical of the foregoing organometallic compounds reactive with said alcohols are methyllithum; n-butyllithium; sec-butyllithium; tert-butyllithium; phenyllithium; phenylsodium; n-amylsodium; diethylzinc; di-n-butylzinc; and the like, and mixtures thereof. Typical of the metallic alkoxides employable are lithium tert-butoxide; lithium 2-methyl-1-pentyloxide; lithium sec-butoxide; sodium tert-butoxide; sodium tert-amyloxide; sodium 2-methyl-1-pentyloxide; potassium tert-butoxide; potassium tert-amyloxide; potassium 2-methyl-1-pentyloxide; tri-n-butoxyboron; tri-2-methyl-1-pentyloxyboron; zinc di-2-methyl-1-pentyloxide; and the like, and mixtures thereof. Such added compounds may and apparently do, form, with the novel magnesium dialkoxides made in accordance with my present invention, complexes with said magnesium dialkoxides.

In a still further embodiment of my present invention, diorganomagnesium compounds are employed which are soluble in liquid hydrocarbon and chlorinated hydrocarbon media for interaction with the magnesium dialkoxides of the present invention. Examples of these diorganomagnesium compounds are diethylmagnesium; n-butyl-ethylmagnesium; di-n-hexylmagnesium; di-sec-butylmagnesium; di-2-methylbutylmagnesium; di-n-octylmagnesium, and the like, and mixtures thereof. These may be added in the range of 0.01 to 100 moles of dialkylmagnesium (per mole of magnesium dialkoxide), but more preferably in the range of 0.1 to 10 moles per mole of magnesium dialkoxide. It is not necessary that the dialkylmagnesium and magnesium dialkoxide compounds be admixed in stoichiometric or even in definite integral relationships (1:2, 1:3, 3:1, 3:2, etc.) to each other since the solutions of these components form mutually miscible products. Products formed by this interaction can be considered to be alkylmagnesium alkoxides, and also can be formed by adding varying amounts of the particular types of alcohols to a dialkylmagnesium compound, according to the present invention.

It is generaly preferable (although not essential) to add organometallic compounds or metallic alkoxides which are soluble in the liquid hydrocarbon and chlorinated hydrocarbon medium employed.

A wide variety of liquid hydrocarbon and chlorinated hydrocarbon solvents can be employed in the practice of the present invention. Generally, such solvents employed are the ones in which the dialkylmagnesium solutions would be sold commercially. However, as mentioned above, additional solvents of choice can be added as diluents for the particular reactive alcohol. Aliphatic or cycloaliphatic solvents, such as, for example, isopentane, n-pentane, n-hexane, n-heptane, cyclohexane, methylcyclohexane, and the like, are preferred. However, aromatic solvents can also be employed, such as benzene, toluene, xylene, mesitylene, and the like, or mixtures thereof with aliphatic or cycloaliphatic solvents. Among the illustrative liquid hydrocarbon and chlorinated hydrocarbon solvents are chloroform; carbon tetrachloride; 1,1,1-trichloroethane; 1,1-dichlorobutane; 1,4-dichlorobutane; 1-chlorohexane; chlorocyclohexane; mono- and polychlorobenzenes; 3,4-di-chlorotoluene; 1-chloropentane; 1,3-dichlorohexane; dichlorofluoromethane; trichlorofluoromethane, and the like.

It is also within the scope of my present invention to employ minor quantities of ethereal solvents in the formulation of the magnesium dialkoxide solutions, such as diethyl ether; THF; methyl tert-butylether; di-n-butylether; and the like, or monofunctional tertiary amines, such as trimethylamine; triethylamine; N-methylpiperidine, and the like, in those instances where, for any particular uses of said solutions, their use is not contra-indicated. Other co-solvents compatible with magnesium dialkoxides can also be employed, such as dimethylacetamide; dimethylformamide; hexamethylphosphorus triamide, and the like. To the extent that they are used, the amounts thereof are generally present in the range of about 5–25% by volume of total solvent used.

The following Examples are illustrative of various facets of the present invention, showing the preparation of novel stable liquid hydrocarbon and chlorinated hydrocarbon solvent-soluble magnesium dialkoxides and complexes thereof. It will, of course, be understood that many other novel stable liquid carbon and chlorinated hydrocarbon solvent-soluble magnesium dialkoxides can be made pursuant to the present invention, utilizing different magnesium dialkoxides, different liquid hydrocarbon solvents or chlorinated hydrocarbon solvents, and different reaction temperatures, etc., without departing from the guiding principles and teachings disclosed herein. All temperatures are recited in degrees Centigrade.

EXAMPLE I

Preparation of Magnesium Bis-(2,3-Dimethyl-3-Pentyloxide

To 10 ml of a 1.5 M solution of n-butyl-sec-butylmagnesium in heptane, there is gradually added, with cooling and vigorous shaking, 10 ml of a solution of 3.49 g (30 mmoles) of 2,3-dimethyl-3-pentanol in heptane. The reaction mixture stays clear throughout the addition. A fluid solution, 0.93 M in magnesium, is obtained.

EXAMPLE II

Preparation of Magnesium Bis-(3,5-Dimethyl-3-Hexyloxide)

To 10 ml of a 1.5 M solution of n-butyl-sec-butylmagnesium in heptane, there is gradually added, with cooling and vigorous shaking, 10 ml of a solution of 3.9 g (30 mmoles) of 3,5-dimethyl-3-hexanol in heptane. When addition of the alcohol is complete, the reaction mixture is centrifuged, resulting in a clear solution 0.97 M in magnesium.

EXAMPLE III

Preparation of Magnesium Bis-(2-tert-Butylcyclohexyloxide)

To a volume of 80 ml, 61.1 g, of a 32.8 wt. % solution of n-butyl-sec-butylmagnesium in heptane, there is added dropwise, with cooling and stirring, 43.13 g (0.267 mmoles) of 2-tert-butylcyclohexanol dissolved in 35 ml of heptane. After stirring for an additional 30 minutes, a clear solution is obtained 0.88 M in magnesium.

EXAMPLE IV

Preparation of Magnesium Bis-(2,6,8-Trimethyl-4-Nonyloxide)

To a solution of 80 ml, 59.8 g, of 32.7 wt. % n-butyl-sec-butylmagnesium in heptane (0.135 mmoles), there is added dropwise, over a 30-minute period, with stirring and cooling below 40°, 50.8 g (0.27 mmoles) of 2,6,8-trimethyl-4-nonanol dissolved in 30 ml of heptane. After stirring for a short while longer, a clear solution is obtained 0.90 M in magnesium.

EXAMPEL V

Preparation of Magnesium Bis-(2,6 Dimethyl-4-Heptyloxide)

To a solution of 100 ml of a 2 M solution of n-butyl-sec-butylmagnesium in chlorobenzene, there is added 60.6 g (0.42 mmoles) of 2,6-dimethyl-4-heptanol (diisobutylcarbinol) dissolved in 50 ml of chlorobenzene. The temperature of the reaction mixture is kept above 40° throughout the addition A cloudy, gel-containing mixture is obtained, which, on heating to 60°, forms a clear, pale yellow solution which is 0.89 M in magnesium.

EXAMPLE VI

Preparation of Magnesium Bis-(2,4-Dimethyl-3-Pentyloxide)

To 50 ml of a 1.69 M solution of n-butyl-sec-butylmagnesium in heptane, there is added 19.64 g (23.7 ml, 169 mmoles) of 2,4-dimethyl-3-pentanol (diisopropylcarbinol) in 16 ml of heptane. The dibutylmagnesium solution is kept below 0° throughout the addition. Near the end of the addition, a precipitate forms which dissolves on warming to room temperature. The clear solution is stripped of solvent on a ROTOVAP unit, and 30 ml of methylcyclohexane is added to the glassy residue. After a short shaking period, the residue dissolves to give a clear solution which is 1.59 M in magnesium.

EXAMPLE VII

Preparation of Alkylmagnesium Alkoxides $R_xMg(OR')_y$ with y/x=3 and 9

R=n-butyl/sec-butyl
OR=2,4-dimethyl-3-pentyloxy (no Al)
(i) $y/x=3$: 10 ml of 1 M n-butyl-sec-butylmagnesium (10 mmoles), plus 2.19 ml of 2,4-dimethyl-3-pentanol (15.6 mmoles)
Result: Product all in solution
(ii) $y/x=9$: 10 ml of 1M n-butyl-sec-butylmagnesium (10 mmoles), plus 2.62 ml of 2,4-dimethyl-3-pentanol (18.7 mmoles)
Result: Product all in solution

EXAMPLE VIII

Preparation of a 5:1 Complex of Magnesium Bis-(2,4,8-Trimethyl-4-Nonyloxide and Dibutylmagnesium)

To 700 ml of a 1.69 M solution (1.183 mmoles) of n-butyl-sec-butylmagnesium in heptane, there is added dropwise, over a 90-minute period, with stirring, 436 ml, 357 g (1.892 mmoles) of 2,4,8-trimethyl-4-nonanol. After stirring for a short while, the resulting clear solution is 1.15 M in magnesium. No solids precipitate on extended storage at room temperature.

The best embodiments of my present invention of which I am presently aware are dependent upon the particular use or uses to which the novel compounds are put, as, for instance, in the preparation of various catalyst systems, such as those for use in the polymerization of olefins. Those novel magnesium alkoxides made according to Examples I, III, IV and V represent the best embodiments of my invention so far as I am presently aware. As to the complexes thereof, excellent embodiments of the invention are those where such magnesium dialkoxides are complexed with lithium or potassium alkoxides, with trialkylaluminums, such as triethylaluminum or TIBAL, or with dialkylmagnesium compounds.

The particularly preferred embodiments of the novel magnesium dialkoxide compounds, and the solutions thereof of my present invention are, as indicated above, generally dependent upon the particular use or uses to which said compounds and their solutions are to be placed. Generally speaking, the particularly advantageous embodiments of my present invention are the aforesaid organic solvent solutions of magnesium dialkoxides which are derived from the $C_5-C_{18}$ beta $C_1-C_4$ alkyl-substituted secondary and tertiary monohydric alcohols, and mixtures thereof with other alcohols, or complexes thereof with triaklylaluminums or aluminum trialkoxides, alkyllithiums, alkali metal alkoxides, or dialkylmagnesiums.

I claim:

1. In a process for the preparation of hydrocarbon or chlorinated hydrocarbon-solvent solutions of magnesium dialkoxides, the steps which comprise reacting a suspension of magnesium metal or magnesium amide, or a solution of a dialkylmagnesium compound, in a volatile hydrocarbon or chlorinated hydrocarbon solvent with an alcohol selected from the group of (a) aliphatic, cycloaliphatic and acyclic $C_5-C_{18}$ beta- and gamma-alkyl-substituted secondary and tertiary monohydric alcohols; or (b) mixtures of said (a) alcohols with $C_3-C_{18}$ aliphatic or cycloaliphatic beta- and gamma-alkyl-unsubstituted secondary or tertiary alcohols; or (c) mixtures of said (a) alcohols with $C_1-C_{18}$ aliphatic primary unsubstituted and 2-alkyl-substituted alcohols; the mole ratios of said (a) to said (b), and said (a) to said (c), alcohols being 1 of said (a) alcohols to 0.1 to 2 of said (b) and/or said (c) alcohols.

2. The process of claim 1, in which the (a) alcohol is at least one member selected from the group of 2,4-dimethyl-3-pentanol; 4-methyl-3-heptanol; 4-methyl-3-hexanol; 3,4-dimethyl-4-heptanol; 2,6-dimethylcyclohexanol; 2-tert-butylcyclohexanol; 2,6-dimethyl-4-heptanol; and 2,6,8-trimethyl-4-nonanol.

3. The process of claim 1, in which the $C_3-C_{18}$ alcohol which is mixed with the (a) alcohol to constitute the (b) mixtures is at least one member selected from the group of isopropanol; sec-butanol; tert-butanol; tert-amyl alcohol; and 3-methyl-3-pentanol.

4. The process of claim 1, in which the $C_1$–$C_{18}$ alcohol which is mixed with the (a) alcohol to constitute the (c) mixture is at least one member selected from the group of methanol; ethanol; n-propanol; n-butanol; n-hexanol; n-octanol; 2-methyl-1-butanol; 2-methyl-1-pentanol; and 2-ethyl-1-hexanol.

5. The process of claim 1, in which the dialkylmagnesium compound is selected from the group of n-butyl-sec-butylmagnesium; n-butyl-ethyl-magnesium; di-n-hexylmagnesium; n-butyl-n-octylmagnesium; and mixed ethyl, butyl, hexyl, and octyl magnesiums.

6. The process of claim 1, in which an excess of said (a) alcohols or said mixtures thereof with said (b) and-/or (c) alcohols, above that necessary to react with all of the dialkylmagnesium present, is employed, the excess of said alcohol or alcohols being in the range of about 0.01 to about 2 moles of alcohol per mole of magnesium reacted.

7. A chemical composition selected from the group of liquid hydrocarbon and chlorinated hydrocarbon solvent-soluble compounds and complexes of (i) $C_5$–$C_{18}$ magnesium aliphatic, cycloaliphatic or acyclic beta- and gamma-alkyl-substituted secondary and tertiary dialkoxides; (ii) mixtures of $C_5$–$C_{18}$ magnesium beta- and gamma-alkyl-substituted secondary and tertiary dialkoxides with minor proportions of $C_3$–$C_{18}$ magnesium aliphatic and cycloaliphatic beta- and gamma-alkyl-unsubstituted secondary dialkoxides; (iii) mixtures of $C_5$–$C_{18}$ magnesium aliphatic and cycloaliphatic beta- and gamma-alkyl-substituted secondary and tertiary dialkoxides with minor proportions of $C_3$–$C_{18}$ magnesium aliphatic and cycloaliphatic beta- and gamma-alkyl-unsubstituted tertiary dialkoxides; and (iv) mixtures of $C_5$–$C_{18}$ magnesium aliphatic, cycloaliphatic or acyclic beta- and gamma-alkyl-substituted secondary and tertiary dialkoxides with minor proportions of $C_1$–$C_{18}$ magnesium unsubstituted and 2-alkyl-substituted primary (normal) dialkoxides.

8. A chemical composition selected from the group of liquid hydrocarbon and chlorinated hydrocarbon solvent-soluble compounds and complexes of (i) magnesium bis-2,4-dimethyl-3-pentyloxide; (ii) magnesium bis-2,6-dimethyl-4-heptyloxide; (iii) magnesium bis-2,6,8-trimethyl-4-nonyloxide; (iv) magnesium bis-2-tert-butylcyclohexyloxide; and (v) magnesium bis-3,4-dimethyl-4-heptyloxide.

9. Organometallic complex compositions soluble in volatile liquid hydrocarbon and chlorinated hydrocarbon solvents comprising: (i) dialkylmagnesium compounds, soluble in hydrocarbon solvents or chlorinated hydrocarbon solvents, in which the alkyl group or groups of said compounds contain from 2 to 18 carbon atoms, reacted with (ii) $C_5$–$C_{18}$ magnesium dialkoxides, the alcoholic moiety of said dialkoxides being derived from alcohols selected from the group of (a) aliphatic, cycloaliphatic and acyclic beta- and gamma-alkyl-substituted secondary and tertiary monohydric alcohols; or (b) mixtures of said (a) alcohols with $C_3$–$C_{18}$ aliphatic secondary or tertiary beta- or gamma-alkyl-unsubstituted alcohols; or (c) mixtures of said (a) alcohols with $C_1$–$C_{18}$ aliphatic primary unsubstituted and 2-alkyl-substituted alcohols; the mole ratios of said (a) to said (b) and said (a) to said (c) alcohols being 1 of said (a) alcohols to 0.1 to 2 of said (b) and/or said (c) alcohols, the ratio of said dialkylmagnesium compounds to said magnesium dialkoxides being in the range of from 1:9 to 9:1.

10. A composition according to claim 9, in which the alkyls of said (a) alcohols contain from 1 to 4 carbon atoms.

11. A composition according to claim 9, in which the (a) alcohol is at least one member selected from the group of 2,4-dimethyl-3-pentanol; 4-methyl-3-heptanol; 4-methyl-3-hexanol; 3,4-dimethyl-4-heptanol; 2,6-dimethyl-4-heptanol; 2,6-dimethylcyclohexanol; 2-tert-butylcyclohexanol; and 2,6,8-trimethyl-4-nonanol.

12. a composition according to claim 10, in which the alkyl is methyl.

13. An organometallic complex composition soluble in hydrocarbon and chlorinated hydrocarbon solvent solutions, said composition being produced by reacting a member selected from the group of lithium alkoxides, sodim alkoxides, potassium alkoxides and mixtures thereof with a magneium dialkoxide resulting from the reaction of magnesium metal, magnesium amide, or a solution of a dialkylmagnesium compound in a volatile hydrocarbon or chlorinated hydrocarbon solvent, with alcohols selected from the group of (a) $C_5$–$C_{18}$ aliphatic, cycloaliphatic and acyclic beta- and gamma-alkyl-substituted secondary and tertiary monohydric alcohols; or (b) mixtures of said (a) alcohols with $C_3$–$C_{18}$ aliphatic, cycloaliphatic and acyclic beta-and gamma-alkyl-unsubstituted secondary or tertiary alcohols; or (c) mixtures of said (a) alcohols with $C_1$–$C_{18}$ aliphatic primary unsubstituted or 2-alkyl-substituted alcohols; the mole ratios of said (a) to said (b) and said (a) to said (c) alcohols being 1 of said (a) alcohols to 0.1 to 2 of said (b) and/or said (c) alcohols.

14. A composition according to claim 13, in which the mole ratio of said lithium alkoxides, sodium alkoxides, and said potassium alkoxides to the said magnesium dialkoxide is in the range of about 0.1 to about 10.

15. Hydrocarbon and chlorinated hydrocarbon solvent-soluble complexes of magnesium dialkoxides with alkali metal alkoxides, said complexes being selected from the group of (i) magnesium bis-2,4-dimethyl-3-pentyloxide and sodium tert-amyloxide; (ii) magnesium bis-2,6-dimethyl-4-heptyloxide and lithium 2-methyl-1-pentyloxide; (iii) magnesium bis-2,6,8-trimethyl-4-nonyloxide and potassium tert-butoxide; (iv) magnesium bis-2-tert-butylcyclohexyloxide and lithium sec-butoxide; and (v) magnesium bis-3,4-dimethyl-4-heptyloxide and lithium sec-butoxide.

16. An organometicallic complex composition soluble in hydrocarbon and chlorinated hydrocarbon solvent solutions, said composition being produced by reacting a member selected from the group of aluminum trialkyls and aluminum trialkoxides, or mixtures thereof, with a magnesium dialkoxide resulting from the reaction of a magnesium metal, magnesium amide, or a solution of a dialkylmagnesium compound in a volatile hydrocarbon or chlorinated hydrocarbon solvent, with alcohols selected from the group of (a) $C_5$–$C_{18}$ aliphatic, cycloaliphatic and acyclic beta- and gamma-alkyl-substituted secondary and tertiary monohydric alcohols; or (b) mixtures of said (a) alcohols with $C_3$–$C_{18}$ aliphatic, cycloaliphatic and acyclic beta- and gamma-alkyl-unsubstituted secondary and tertiary alcohols; or (c) mixtures of said (a) alcohols with $C_1$–$C_{18}$ aliphatic primary unsubstituted or 2-alkyl-substituted alcohols; the mole ratios of said (a) to said (b) and said (a) to said (c) alcohols being 1 of said (a) alcohols to 0.1 to 2 of said (b) and/or said (c) alcohols.

17. A composition according to claim 16, in which the mole ratio of said aluminum trialkyls or aluminum trialkoxides to the said magnesium dialkoxide is in the range of about 0.1 to about 10.

* * * * *